(12) United States Patent
Delmotte (10) Patent No.: US 8,753,670 B2
(45) Date of Patent: Jun. 17, 2014

(54) FIBRIN FOAM AND PROCESS

(75) Inventor: Yves A. Delmotte, Neufmaison (BE)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1446 days.

(21) Appl. No.: 12/055,516

(22) Filed: Mar. 26, 2008

(65) Prior Publication Data

US 2009/0246260 A1   Oct. 1, 2009

(51) Int. Cl.
| | |
|---|---|
| *A61F 13/00* | (2006.01) |
| *A61L 15/16* | (2006.01) |
| *A61L 15/00* | (2006.01) |
| *A61K 9/70* | (2006.01) |
| *A61K 38/36* | (2006.01) |
| *A61K 35/14* | (2006.01) |
| *C07K 14/745* | (2006.01) |

(52) U.S. Cl.
USPC ........... 424/443; 424/444; 424/445; 424/446; 424/447; 435/13; 514/13.5; 514/13.6; 514/13.7; 530/382; 604/82; 604/92; 604/416; 606/214

(58) Field of Classification Search
None
See application file for complete search history.

(56) References Cited

U.S. PATENT DOCUMENTS

| | | | |
|---|---|---|---|
| 2,492,458 A * | 12/1949 | Bering, Jr. .................... | 424/443 |
| 3,861,652 A | 1/1975 | Clark et al. | |
| 4,359,049 A * | 11/1982 | Redl et al. ........................ | 604/82 |
| 4,631,055 A | 12/1986 | Redl et al. | |
| 4,846,405 A | 7/1989 | Zimmermann | |
| 4,978,336 A | 12/1990 | Capozzi et al. | |
| 5,116,315 A | 5/1992 | Capozzi et al. | |
| 5,318,524 A * | 6/1994 | Morse et al. .................... | 604/82 |
| 5,368,563 A | 11/1994 | Lonneman et al. | |
| 5,443,183 A | 8/1995 | Jacobsen et al. | |
| 5,474,540 A | 12/1995 | Miller et al. | |
| 5,582,596 A | 12/1996 | Fukunaga et al. | |
| 5,605,255 A | 2/1997 | Reidel et al. | |
| 5,665,067 A | 9/1997 | Linder et al. | |
| 5,989,215 A | 11/1999 | Delmotte et al. | |

(Continued)

FOREIGN PATENT DOCUMENTS

| | | |
|---|---|---|
| DE | 203 07 153 U1 | 9/2003 |
| WO | 96/39212 | 12/1996 |

(Continued)

OTHER PUBLICATIONS

U.S. Appl. No. 11/624,113, filed Jan. 17, 2007, Baxter International Inc.

(Continued)

*Primary Examiner* — Daniel Sullivan
*Assistant Examiner* — Dominic Lazaro
(74) *Attorney, Agent, or Firm* — K&L Gates LLP (57) ABSTRACT

A fibrin wound dressing is made by mixing quantities of fibrinogen solution and thrombin solution with air. The resulting foam is very light weight, and with the proper attention to the amount of thrombin, is also sufficiently viscous to rest on a vertical surface without dripping. The wound dressing may also be formulated for its ability to continue migration of healing substances, such as PDGF, from the dressing to the wound site. Thrombin substitutes, such as other clotting proteins, may be used instead of thrombin. The resulting foam may also be lyophilized or ground and lyophilized for later reconstitution. A therapeutic drug or other additive may also be added to the wound dressing.

8 Claims, 3 Drawing Sheets

(56) References Cited

U.S. PATENT DOCUMENTS

| | | | |
|---|---|---|---|
| 6,132,396 | A | 10/2000 | Antanavich et al. |
| 6,328,229 | B1 | 12/2001 | Duronio et al. |
| 6,454,739 | B1 | 9/2002 | Chang |
| 6,461,361 | B1 | 10/2002 | Epstein |
| 6,548,729 | B1 | 4/2003 | Seelich et al. |
| 6,585,696 | B2 | 7/2003 | Petersen et al. |
| 6,620,125 | B1 | 9/2003 | Redl |
| 6,802,822 | B1 | 10/2004 | Dodge |
| 6,884,232 | B1 | 4/2005 | Hagmann et al. |
| 6,921,381 | B2 | 7/2005 | Spero et al. |
| 7,135,027 | B2 | 11/2006 | Delmotte |
| 2003/0146113 | A1 | 8/2003 | Unkrig et al. |
| 2006/0009801 | A1 | 1/2006 | McGurk et al. |

FOREIGN PATENT DOCUMENTS

| | | | |
|---|---|---|---|
| WO | 2004/024306 | A1 | 3/2004 |
| WO | 2005/048977 | A | 6/2005 |
| WO | 07/084919 | | 7/2007 |
| WO | 2007/084919 | A1 | 7/2007 |
| WO | 2009/083544 | | 7/2009 |

OTHER PUBLICATIONS

Porvair Filtration Group Ltd, "Developments in porous polymeric materials", Press Release, Sep. 2005, Fareham, Hampshire UK.

Porex Porous Products Group, "Products & Services", catalog, www.porex.com, Fairburn, GA.

Porex Porous Products Group, "Mupor(tm) Membrane Applications Brief", catalog, www.porex.com, Fairburn, GA.

Porex Porous Products Group, "Interact W/Innovation . . . discover the advantages of Porex", catalog, www.porex.com, Fairburn, GA.

Porvair Filtration Group, "Sintered Porous Materials", catalog, www.porvairfiltration.com, Fareham, Hampshire UK.

Merck Index, "No. 7498", 9th edition, p. 996.

Shanbrom, E. et al., "Total Fibrin 'Super Glue' Components From Human Plasma: A New Blood Banking Procedure", Journal of Thrombosis and Haemostasis, Aug. 1, 2007, vol. 5, Supplement 1, Acta Physiologica Congress, Oxford, UK.

Andras Gruber et al., "Alteration of Fibrin Network by Activated Protein C", Blood, May 1, 1994, pp. 2541-2548, vol. 83, No. 9.

Matras, Helene, "Fibrin Seal: The State of the Art", J Oral Maxillofac Surg, 1985, vol. 43, pp. 605-611, W.B. Saunders Co., Philadelphia, PA.

Gibble J.W. et al., "Fibrin glue: the perfect operative sealant?", Transfusion, 1990, vol. 30, No. 8, pp. 741 to 747, Baltimore MD.

International Search Report and Written Opinion for International Application No. PCT/US2009/034842 dated May 26, 2010.

Notification of Transmittal of the International Preliminary Report on Patentability for International Application No. PCT/US2009/034842 dated Oct. 8, 2010.

* cited by examiner

FIBRIN FOAM AND PROCESS

BACKGROUND

The invention is in the field of medical science and surgery, and in particular in the field of wound dressings. Foaming of combined fluid streams, including fluid streams of different viscosities, may be useful in a wide variety of settings including the medical field, the food industry, electronics, automotive, cosmetic, energy, petroleum, pharmaceutical, chemical industries, manufacturing and others. In the fuel or energy industries, inline mixing of air, water or other components with fuel may be helpful to increase engine yield, create environmentally safer or cleaner fuels.

It has been known for some time that mixtures of fibrinogen and thrombin may be applied to wounds, such as open wounds of a person, to close the wound, stop the bleeding, and prevent other substances, such as infectious agents, from entering the wound. Fibrin is a well known tissue sealant that is made from a combination of at least two primary components, fibrinogen and thrombin, which have viscosities that depend greatly on the temperature. For example, the viscosity of fibrinogen varies from about 350 cst at 15° C. to less than 100 cst at 37° C. Upon coming into contact with each other, the fibrinogen and thrombin interact to form a tissue sealant, fibrin. The quality of the fibrin generated will substantially depend on the completeness of the mixing of the two components.

Fibrinogen and thrombin are generally provided in lyophilized form and stored at very low temperatures. Lyophilized fibrinogen is typically reconstituted with sterile water before use. Thrombin is also reconstituted with sterile calcium chloride or water, such as distilled water, before use. Saline, phosphate buffered solution (PBS), or other reconstituting liquid can also be used. In preparing fibrin, the reconstituted fibrinogen and fibrin are then combined to form fibrin.

In-line mixing techniques have been discovered for mixing thrombin and fibrinogen to from a wound sealant. The sealant may be applied by a dispenser that ejects the sealant directly onto the tissue or other substrate or working surface. Examples of tissue sealant dispensers are shown in U.S. Pat. Nos. 4,631,055, 4,846,405, 5,116,315, 5,582,596, 5,665,067, 5,989,215, 6,461,361 and 6,585,696, 6,620,125 and 6,802,822 and PCT Publication No. WO 96/39212, all of which are incorporated herein by reference. Further examples of such dispensers also are sold under the Tissomat® and Duploject® trademarks, which are marketed by Baxter AG.

Typically, in these prior art devices, two individual streams of the fibrinogen and thrombin components are combined and the combined stream is dispensed to the work surface. Combining the streams of fibrinogen and thrombin initiates the reaction that results in the formation of the fibrin sealant. The liquid fibrin sealant is frequently referred to as a fibrin gel. While thorough mixing is important to fibrin formation, fouling or clogging of the dispenser tip can interfere with proper dispensing of fibrin. Clogging or fouling may result from contact or mixing of the sealant components in the dispenser and the formation of a significant quantity of viscous fibrin in the passageway prior to ejection of the components from the dispensing tip.

This clogging may result from using a high concentration of thrombin, such as 250 IU/ml. As is clear from the clogging, high concentrations of thrombin result in a much faster setting time, but may also result in incomplete mixing and binding between the thrombin and the fibrinogen, and thus an incomplete formation and release of fibrin to enable clotting. If the formulation also includes growth factor, such as platelet development growth factor (PDGF), it is believed that a high thrombin concentration causes poor binding of the growth factor to fibrin and therefore a poor release into the wound, where it would otherwise help to control clotting and tissue healing over time. Failure to clot as a result of the fibrin sealant curing too quickly may lead to further bleeding, causing additional loss of blood from the wound, and at a minimum delaying healing of the wound and possibly requiring further attention from a medical professional.

Curing too quickly thus may impede clotting and delay healing of the wound. However, the curing may also occur too slowly, such as when low concentrations of thrombin are used. If the sealing compound does not cure and become firm reasonably quickly, the sealing compound may fall away or drip from the wound. If blood or other body fluids are involved, this creates a very unsightly and potentially hazardous condition. If the compound has fallen away from the wound site, and is not present, it cannot help to seal the wound or release fibrin into the wound to encourage clotting.

One innovation to solve these problems has been to mix air with one or the other of fibrinogen or thrombin, as seen in U.S. patent application Ser. No. 11/624,113, filed Jan. 17, 2007, which is assigned to the assignee of the present patent, and which is hereby incorporated by reference. This patent application proposes mixing aqueous fibrinogen at about 100 mg/ml concentration in one container, with another container having 2.5 ml thrombin at about a 4 IU/ml concentration and 2.5 ml air. The mixing technique includes transferring the components back and forth several times, at least two times, to create a fibrin foam. This foam has a relatively higher volume of air and, of course, a low density, a low concentration of fibrinogen and thrombin per unit volume, and a resulting low concentration of fibrin per unit volume in the foam. This low concentration results in a very long setting time to create a fibrin network. The drawback is that the conventional procedure to make a fibrin glue remains a technique based on use of equal volumes of fibrinogen and thrombin. The main feature of the foam is its low density, and therefore it is important to reduce the volume of diluent used or to increase the percentage of air in the foam formulation, or both.

What is needed is a better way to formulate wound dressings that will yield a firm, adherent wound dressing while controlling clotting and tissue healing.

SUMMARY

One embodiment is a wound dressing made of a fibrin foam. The wound dressing includes a quantity of fibrinogen, a quantity of a clotting protein, and a quantity of air mixed with the fibrinogen and the clotting protein, wherein the quantity of fibrinogen comprises a water solution with a concentration of fibrinogen and the quantity of clotting protein comprises a water solution with a concentration of a clotting protein, and wherein the wound dressing comprises a first foam made by mixing the quantity of fibrinogen with a portion of the quantity of air and further comprises a second foam made by mixing the quantity of the clotting protein with a remainder of the quantity of air, and mixing the first and second foams to form a wound dressing, wherein the wound dressing is sufficiently firm to adhere to a vertical surface. In another embodiment, the quantity of fibrinogen, the quantity of thrombin, and the quantity of air are configured for mixing in an apparatus capable of being held in a hand or hands of a user.

Another embodiment is a wound dressing. The wound dressing includes a quantity of aqueous fibrinogen, a quantity of aqueous thrombin, and a quantity of gas, wherein the quantity of aqueous fibrinogen and the quantity of aqueous thrombin are configured for separate mixing with portions of the quantity of gas in a hand-held mixing container, and are configured for mixing together to form a foamed wound dressing which is sufficiently viscous to adhere to a vertical surface.

Another embodiment is a method of applying a wound dressing. The method includes steps of combining a first liquid wound dressing component with air in a hand-held mixing device, combining a second liquid wound dressing component with air in a hand-held mixing device, mixing the first liquid wound dressing component combined with air and the second liquid wound dressing component combined with air to form a fibrin foam, and applying the fibrin foam to a surface, wherein the fibrin foam has a viscosity sufficient for a thin coating of the fibrin foam to adhere to a vertical surface. This viscosity is estimated at about 10 centipoise (cps).

Another embodiment is a method for forming a fibrin foam. The method includes steps of combining a solution of fibrinogen with air to form a first foam, combining a solution of a clotting protein with air to form a second foam, and mixing the first and second foams to form a fibrin foam, wherein the fibrin foam has a viscosity sufficient for a thin coating of the fibrin foam to adhere to a vertical surface.

Additional features and advantages are described herein, and will be apparent from, the following Detailed Description and the figures.

DETAILED DESCRIPTION

Fibrinogen is cleaved and polymerized into fibrin using thrombin in a well-characterized process. Thrombin, a protease or enzyme, cleaves fibrinogen, forming fibrin monomers. Once the fibrinogen is cleaved, a self-assembling step occurs in which the fibrin monomers come together and form a covalently crosslinked fibrin network in the presence of Factor XIII, normally present in blood. In the presence of calcium, thrombin transforms Factor XIII into Factor XIIIa, forming a proteinaceous network. This helps to close the wound and promote healing of the site. The fibrin network forms an excellent wound dressing which is applied to a wound site on a patient, such as a surgical field. Using the techniques described herein, thrombin concentrations from 5 to 20 IU/ml may be used if both components are used at reduced temperature, such as 15° C. Thrombin concentration may be as high as 500 IU/ml if the concentration of fibrinogen is decreased to a very low level, such as 3 mg/ml.

Foamed Product

It has now been unexpectedly discovered that one way to increase the surface area of the wound dressing available to the site is to formulate the fibrin as a foam, with very low density and very high surface area. This may be accomplished by separately and repeatedly mixing the principal components with air, and then combining all the components, so that the resultant mixture is a stable foam. The foam may then be applied to the wound. With appropriate mixtures of fibrinogen and thrombin, the foam is sufficiently stable and viscous, so that it is retained even when applied on a vertical surface. In making these mixtures, fibrinogen and thrombin were used. Mixtures of fibrinogen may be furnished in aprotinin aqueous solution. Mixtures of thrombin include a solvent or carrier. The amount of thrombin is actually quite small as a percent of volume, and is usually designated as a specific quantity of International Units (IU) or IU/ml. For purposes of this patent, a water solution of any of these components includes saline, PBS, or other solutions in which water is the principal component.

Figure 1:
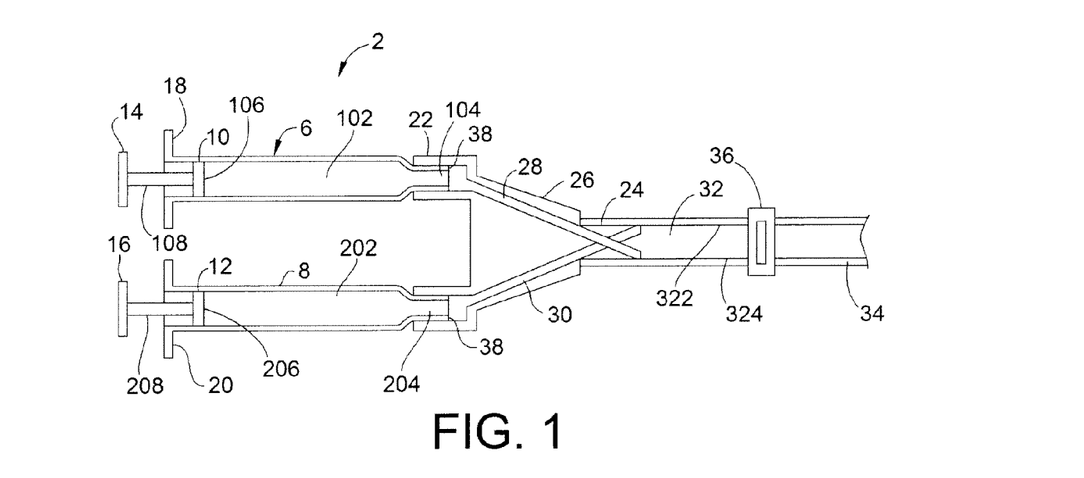
FIG. 1 is a first embodiment of a hand-held mixing device.

Numerous experiments were conducted for better mixing of the wound dressing components with hand-held dual mixing chambers, the chambers arranged side-by-side. FIG. 1 depicts a dispenser 2 for mixing at least two components of a combined fluid stream, such as a sealant, or tissue sealant or other combined fluid stream. Although the dispensers, systems and methods are generally illustrated and described in the context of a tissue sealant dispenser, it is understood that embodiments are not limited to such a dispenser or to the mixing of tissue sealant components, and that there are applications in a variety of settings where mixing of component fluid streams is desired.

As shown in FIG. 1, dispenser 2 includes at least two fluid component sources, illustrated in the form of hollow cylinders or barrels 6 and 8, although other source containers from which fluid components are provided may be used. In the embodiment of FIG. 1, each barrel has a generally cylindrical interior or bore in which one of the fluid components such as fibrinogen or thrombin for forming fibrin tissue sealant is stored. The distal end of each barrel has an outlet port 38 for communicating with a dispensing tip 22.

The bore of each barrel 6, 8 slidably receives a distal end of a piston or plunger 10, 12, respectively, for ejecting the sealant component from the respective bore. A driving portion 14, 16 for a user's thumb is associated with each plunger and extends proximally from the distal portion. A finger grip or finger rest 18, 20 is associated with each barrel 6, 8 and may be actuated or pushed manually or automatically to eject the component. The finger-grips 18, 20 may be actuated either independently or simultaneously, such as by a common actuator or yoke that couples the plungers together for simultaneous movement. Materials for syringes may include polyethylene, polypropylene, cyclic olefin copolymers (COC), and other suitable materials. The plungers or pistons, or at least their tips, may be made from an elastomer, such as silicone. Alternatively, silicone may be eliminated in the plungers if they are made from a less expensive material, such as thermoplastic elastomer, and then coated with a fluorinated coating, such as Fluorotec®, or others available from Dalkyo Seiko, Ltd., of Tokyo, Japan.

The illustrated tip assembly or structure is a multi-part assembly and includes a flow director 26. The flow director 26 has a proximal end 22 and a distal end 24 and defines respective first and second passageways 28 and 30. Each passageway 28, 30 communicates with a respective bore of the barrels 6, 8 to allow the respective component to exit the distal end 24. The inlet to each passageway 28 and 30 is suitable for attachment to one of the outlets from barrels to 6, 8 such as, for example, by a luer fitting or other attachments as will be apparent to persons of skill in the relevant field. It is contemplated that embodiments are not limited to dispensers for sealant and may be used to combine two or more components for other combined fluid streams for other applications within or outside of the medical field.

Each of the first and second passageways 28, 30 communicates with one of the components as a separate fluid stream until such streams approach or are at the distal end 24. As shown in FIG. 1, the first and second passageways 28, 30 may be non-parallel and non-intersecting relative to one another such that they direct each component stream into a combined third passageway 32 at an angle that may assist combination of the two streams. For example, as shown in FIG. 1, the passageways are separate (with one passageway 28 or 30 being located offset and non-intersecting to the other) until the streams exit their respective passageways. In FIG. 1, the exiting streams are initially directed away from each other, towards opposed inner surfaces of the third passageway 32 which will deflect the separate stream and cause them to converge before they encounter in-line mixer 36, described below, and then exit through distal end 34. The flow of the fluid component streams in the third passageway 32 may be turbulent or otherwise provide fluid flow conditions which result in some mixing of the exiting streams of fluid components in this region.

In-line mixer 36 is a thin disc or cylinder, a three-dimensional lattice or matrix with a plurality of tortuous, interconnecting passages therethrough. By forcing two streams through such a mixer, intimate, thorough mixing is achieved. These mixers are described in U.S. patent application Ser. No. 11/624,113, later published as U.S. Publication No. 2009-0246260 on Oct. 1, 2009, which was co-pending at the time of this application, assigned to the assignee of the present patent document, and which is hereby incorporated by reference in its entirety. These discs are typically 1-3 mm in thickness and have a pore size from about 5-300 micrometers. The porosity is generally from about 20-40%, and the diameter is such that a sufficient flow rate and mixing rate may be achieved using pressure available from the mixing equipment and finger-or-thumb generated pressures. The in-line mixers are typically made from sintered polyethylene or polypropylene and are generally hydrophobic in nature. These materials are available commercially from Porvair Filtration Group, Ltd., Hampshire, UK, or Porex Corp., Fairbum, Ga., U.S.A.

Figure 2:
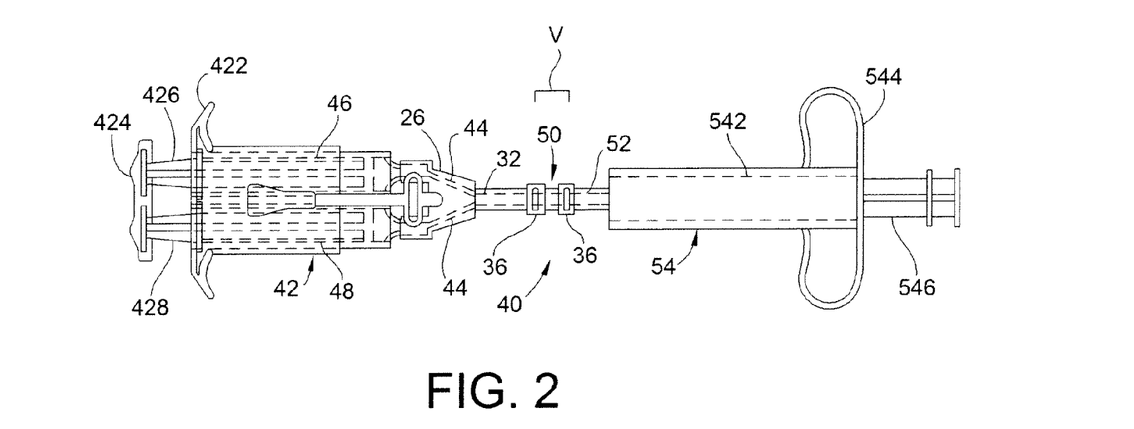
FIG. 2 is a second embodiment of a hand-held mixing device.

Opposed chambers as depicted in FIG. 2 may also be used. The mixing device 40 shows equipment for mixing of at least two separate components employing an in-line mixer connector 50, which may be attached at one end to a first mixer device having two separate containers or syringes 46 and 48, respectively, and attached at its other end to a syringe 54. The joined syringes 46, 48 have joined plungers 426, 428 with a common driving portion 424 and a joined finger grip 422. As noted above, the components may be allowed to flow from the separate containers 46 and 48 through corresponding separate passageways 44 in flow director 26 to a combined passageway 32 which extends to the in-line mixer connector 50. The mixture of the components flows through in-line mixer connector 50 having two inline mixers 36, separated by a distance V, the inline mixers positioned therein adjacent a passageway 52 of syringe 54 attached to the opposite side of in-line mixer connector 50 for dispensing as desired. Syringe 54 includes a barrel or chamber 542, grip 544, and plunger 546. In this example, the inline mixers have a separation distance V of between about 0 and 5 mm. Other embodiments are between about 3 and 4 mm apart. Other distances may be used.

In work done to date, temperature has had little effect on mixing. Foams have been made from fibrinogen and thrombin as described below at 4° C., 18°, 27° and 37°. Because of this remarkable ability, the fibrinogen and thrombin do not need to be pre-warmed before they are mixed in operating rooms, which are normally between about 18 to 22° C. This may be because of the inherent low thermal capacity of foams, as compared to full-density liquids or mixtures.

The components may be kept in sterile packages, double blister packs. Operating room personnel need only unpack the outer blister pack and transfer the inner blister pack, sterile inside and out, to the sterile nurse. The fibrinogen solution is held in a first container, which may be a sterile hand-held mixer as disclosed herein, or may be a different container. The solution of thrombin or other clotting protein is held in a second container, which may be a portion of the sterile hand-held mixer as disclosed herein, or may be another container. The sterile nurse then prepares the fibrin foam for the surgeon. This eliminates the need for a circulating nurse to warm and reconstitute the foam, since the sterile nurse can easily and quickly mix the foam, no pre-warming needed, with embodiments as described herein.

Additional Mixing Methods

Figure 3:
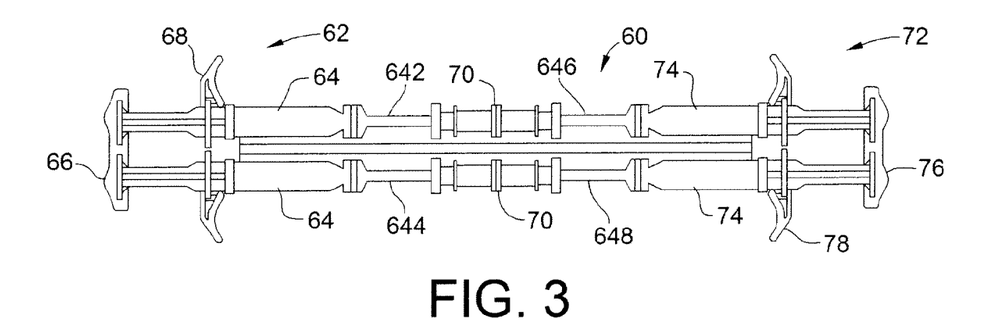
FIG. 3 is a third embodiment of a hand-held mixing device.
Figure 4:
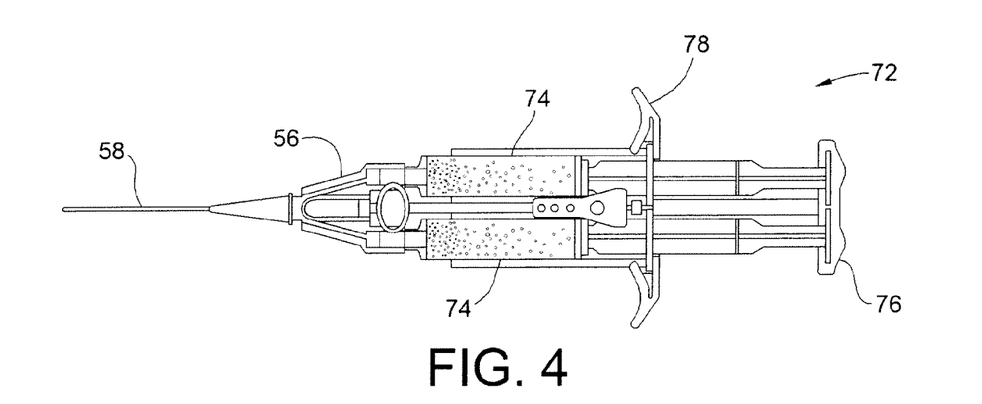
FIG. 4 is another embodiment of a hand-held mixing device.

The experiments discussed above were also conducted with both side-by-side and opposed chambers, as depicted in FIGS. 3 and 4. FIG. 3 depicts a device in which both components are foamed individually and then placed in individual syringe bodies. FIG. 4 depicts one of the double-chamber mixing devices and a Y connector for use in mixing and dispensing the foam.

The embodiment of FIG. 3 includes two pairs of opposed chambers. Mixing device 60 includes a left side 62 with first and second chambers 64 and joined plungers 66, and a right side 72 with first and second chambers 74 and joined plungers 76. The left hand side 62 includes a finger rest or grip 68, and the right hand side includes a finger rest or grip 78. In use, one of the chambers 64 on the left may include a quantity of liquid fibrinogen solution and the other chamber 64 on the left may include a quantity of liquid thrombin solution. Chambers 74 on the right each contain a quantity of air. When a user grasps either finger grip 68, 78 and depresses with plunger 66 or 76, the materials in that side are forced through the connectors and inline mixers 70, which have been described above. Several sequential plunges back and forth insure excellent mixing of both components. Of course other components may also be used, as outlined below, to enhance the performance of the foam produced.

When the components have been mixed thoroughly, the components will end up on either the left side or the right side. The two components, in this example foamed fibrinogen and foamed thrombin, each necessarily mixed with air (or other gas), then need to be mixed together. A device for accomplishing this mixing is depicted in FIG. 4. The mixing device 72 of FIG. 4 is simply the left side or right side of the embodiment of FIG. 3, in this example the right side. To this device is added a Y-connector 56 and a dispensing needle 58. The Y-connector is similar to the one depicted in FIG. 1, but no inline mixer is used. In other embodiments, an inline mixer may also be used between the Y-connector and the needle. In place of a needle, a cannula, catheter, spray head, or other type of dispensing device may be used, depending on the application and on the desired form in which the combined mixture is to be applied to the patient.

These experiments included quantities of air in the chambers, as explained herein. In one experiment conducted with the opposed chambers of FIG. 3, a first chamber was filled with 1 ml fibrinogen and a second chamber side by side with the first chamber was filled with 1 ml thrombin. The opposed chambers each had 1 ml air. Thus, air was present at about 50% of the initial volume. There was a small flat, cylindrical inline mixing device in each of the two mixing paths. The inline mixing device was a single disc of Vyon F (supplied by Porvair, UK), connected with standard female luer connectors. As discussed below, other materials may also be used for an inline-mixer, depending on the viscosity of the liquids, so long as the materials have sufficient permeability and porosity to manage flow rates and backpressure at the same time. Mixing was conducted by actuating the joined side-by-side plungers together, sending the fibrinogen and thrombin into the air in the cylinders of the other side, and creating a mixture of the component with air. The actuators on the other side were then actuated, sending the mixtures back into the chambers originally holding the fibrinogen and thrombin. After several mixing operations back and forth, the combinations began to look like foam, a uniform mixture of tiny bubbles. Mixing should be done for at least 2-10 repetitions; better mixing may be attained with 4-10 repetitions.

The mixed products or foams ended up in the right-hand side chambers as shown in FIG. 3. The female luer connectors were then removed and a Y-piece was used to connect the two remaining right-hand chambers, as shown in FIG. 4. In order to deliver the wound dressing, the plungers are depressed and the wound dressing is delivered through the Y-piece and the cannula. The surgeon or surgical assistant may now deliver a wound dressing as desired, since the foam will remain standing, without dripping or oozing, from the site. It is also possible to form a foam in each of two cylinders separately, and then combine them as shown in either FIG. 3 or FIG. 4. As will also be apparent to one having skill in the art, other components may also be added in either of two cylinders, or in a third cylinder, so long as a fibrinogen foam and a thrombin foam are generated before the fibrinogen and thrombin are combined.

Figure 5:
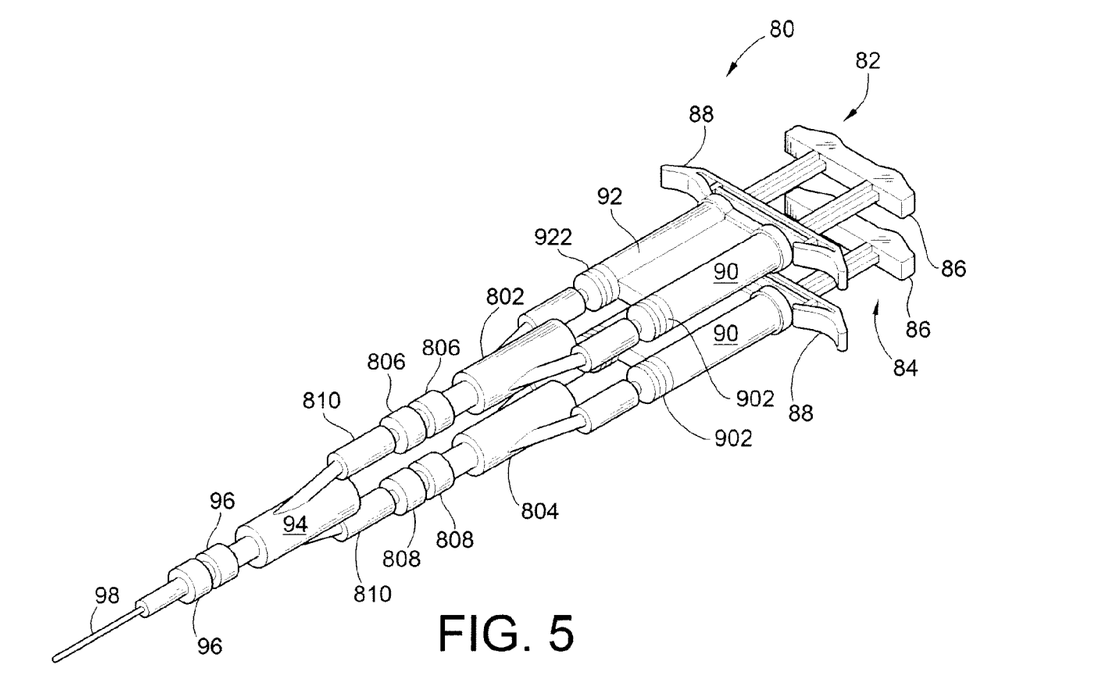
FIG. 5 is another embodiment of a hand-held mixing device.

Other ratios of components may be used to generate fibrin foams using the syringes of FIGS. 3-4 or FIGS. 5-6. FIG. 5 depicts a dual duploject instrument 80 suitable for generating fibrin foam. In FIG. 5, dual duploject syringes 82, 84 are identical, each including side-by-side or adjacent chambers 90, 92 each with a plunger 86 that is joined at the proximal or outside end. Each syringe 82, 84 has a finger rest 88 for restraining the chambers when plunger 86 is actuated by a thumb or other finger of a user. Adjacent chambers 90, 92 are joined on their distal ends by a Y-connector 94 that mixes the streams or fluids injected into the Y from the chambers. The Y-connectors each include two spaced in-line mixers 96, spaced a set distance apart, for thoroughly mixing the two components, i.e., air and a liquid component to form a foam, such as a fibrinogen foam and a thrombin foam, as discussed above. The ends of the dual mixing device portions are then joined with a third Y-connector 94, transverse to the first two Y-connectors. This third Y-connector receives the two foamed components and mixes them again with two additional in-line mixers 96, forming a fibrin foam on the spot for immediate use by the surgeon or other medical professional. The third Y-connector includes a dispensing needle 98 for applying the fibrin foam to a wound, such as a surgical wound on a patient.

As shown in FIG. 5, there are two inline mixers 96 positioned downstream from the syringe chambers where the separate component streams are initially allowed to flow together, although they may also be positioned further upstream, where the streams join. It is contemplated that the distance may vary depending on the design requirements and extent of mixing that is required. By way of example, in handheld syringes of type shown in FIG. 5 for use in fibrin foam delivery, the distance may range between about 0 and 6 mm or from between about 1 and 6 mm. Generally speaking, the homogeneity of fibrin foam created by the illustrated inline mixer decreases with a decrease in the distance, such as 4 mm and less. A distance of between about 5 and 6 mm (about ¼ inch) works well, although other distances are also possible. The mixing devices themselves are spaced apart each other from about 2 mm (0.08 inches) to about 20 mm (0.80 inches).

Figure 6:
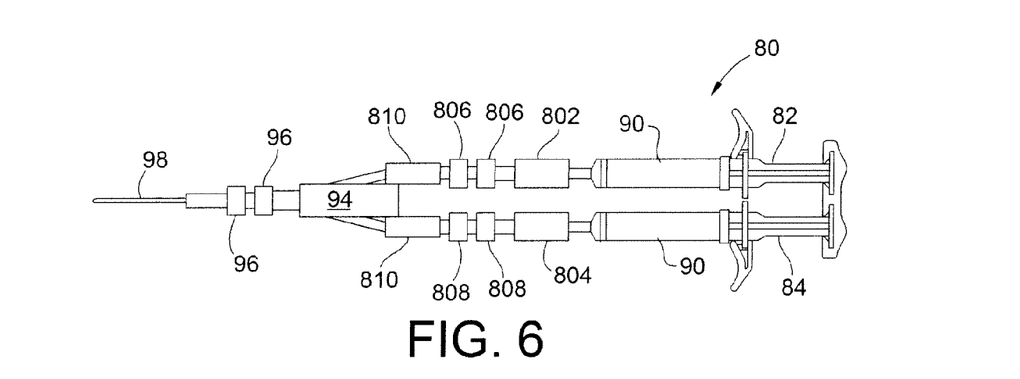
FIG. 6 depicts a side view of the embodiment of FIG. 5.

A side view of the mixing portion is seen in FIG. 6. Upper duploject 82 and its Y-connector 94 and lower duploject 84 and its Y-connector 94 each connect in series to two mixers or mixing devices 96, using luer or other suitable connectors. A third, transverse Y-connector 94, which may be the same as the other Y-connectors or may be different, connects to the mixing devices 96 from the upper and lower duploject syringes. Third Y-connector 94 also includes two mixing devices 96 in series, and also includes a stainless steel dispensing needle 98. While two mixing devices in series are used, one may also be used, and more than one may also be used. Two have worked well.

In another experiment, suitable for the duploject instruments of FIGS. 3-4 or FIGS. 5-6, one container or syringe was filled with 0.5 ml fibrinogen, and another syringe was filled with 0.5 ml thrombin solution. The chambers adjacent each contained 1.0 ml air. In this combination, air was thus present at the start at about 66% of the total volume, and the liquids were present at about 34%. The two were mixed by alternately depressing one plunger and then the other, for a total of 7 mixing actuations. The resulting fibrin foam was very similar to that produced by the devices of FIGS. 3-4, creating fibrinogen foam and thrombin foam before combining the foams. The resulting foams had a density as low as 0.37 g/cc, held their shape and had excellent properties. In contrast, gels formed by mixing 0.5 ml fibrinogen and 0.5 ml thrombin have a density of about 1 g/cc.

As noted above, a wound dressing may be made using a liquid with a very low concentration of fibrinogen if a sufficiently high concentration of thrombin is also used. Thus, this technique for making fibrin foam also allows the use of blood, with concentrations of fibrinogen as low as about 2-4 mg/ml. Blood plasma or even recombinant fibrinogen may also be used, provided sufficiently high concentrations of thrombin are also used.

Another advantage of using the foamed structure is that less product needs to be used per application, and a smaller amount of drug needs to be applied to the patient. For instance, if a surgeon or medical professional is preparing a wound dressing, it is customary to estimate a volume of the dressing to prepare. If the volume calculated is 1 ml, then 1 ml of a gel would be prepared. For a foam, however, the volume of air for the mixture may be included in the total. Thus, a formula for fibrin foam may include proportions of 1 part fibrinogen, 1 part thrombin, and 2.5 parts air (55 volume percent air). If 1 ml of foamed wound dressing is needed, then 0.55 ml air is needed, along with 0.22 ml fibrinogen and 0.22 ml thrombin. This wound dressing will use a smaller volume of components and will be less expensive. Any drug or medicine included in the formulation may also be present in a smaller amount or proportion. This will also result in the application of a smaller amount of medicine to the patient.

Once the fibrin foam according to the above teachings has been made, it is stable. The network has been formed, and the open-cell microstructure has been achieved. Of course, the liquid portion of the foam is still at least 95% water, whether the water is present as saline, phosphate buffered solution, or other source of water. Thus, instead of applying the foam directly, it may be processed for future use by lyophilizing it for more convenient storage and transport. The foam may be lyophilized in the form of a sponge, in the form of beads partially or completely polymerized, or ground to obtain a haemaostatic powder (dry fibrin glue), as described in U.S. Pat. No. 7,135,027, which is hereby incorporated by reference in its entirety. The foam or lyophilisate may then be reconstituted later by addition of water or suitable solution. The mixers described herein may be used for this purpose, by placing the powder into the container and aspirating saline, water, phosphate buffered solution (PBS) or other reconstituting liquid into the mixer and then proceeding.

In the embodiments using the lyophilization process, the lyophilized foam may be made by a relatively simple process, such as by forming the foam using only fibrinogen and thrombin (and air or other gas). When reconstituting the foam, additional components may be added in the ratio or proportion desired, such as additional thrombin, calcium source, FXIII, antibiotics, drugs, any of the many helpful agents listed herein, or other additive desired. This allows the surgeon or medical professional to tailor the wound dressing to the patient, while not requiring the hospital or care center to stock a great variety of lyophilized foams. Embodiments are able to take advantage of a very simple process for forming a foam, the process involving on-the-spot, gentle mechanical mixing, and not requiring expensive laboratory mixing equipment, such as a homogenizer with intensive mechanical stirring, not requiring a vacuum, and not requiring separate gases, as disclosed in U.S. Pat. No. 6,548,729.

Foam Properties as Measured by Standard Tests

Fibrinogen contains selected amounts of alpha ($\alpha$) monomer chain, albumin, beta ($\beta$) chain and gamma ($\gamma$) chain. After mixing with thrombin to form fibrin foam, the resulting fibrin contains different amounts of such component chains due to the crosslinking, and other possible reactions, that have occurred. Typically, fibrin contains a reduced amount of alpha monomer and gamma monomer chains, which have polymerized into alpha-alpha pairs or polymers and gamma-gamma pairs or polymers (or gamma dimer) chains. By way of example and not limitation, the degree or rate of crosslinking may measure the amount of reduction in the alpha monomer chain that is present in the fibrin mixture as compared to the amount of alpha monomer that is present in the fibrinogen prior to mixing.

The degree of crosslinking may for example, measure a selected amount of a constituent component chain that is contained in the fibrin mixture for crosslinking to a selected amount of the same constituent component in fibrinogen. Thus, the degree of crosslinking may be used to show that two particular fibrins are equivalent, in the sense that the degree of crosslinking suggests that one structure is very similar to another. In this instance, one fibrin is made by mixing components in one manner, making a traditional gel, while the other fibrin is made by mixing the components in a different manner, making a foamed structure.

Foams made by the processes described above had properties equivalent to fibrin gels, with equivalent total protein released when urokinase was used, and also showing equivalent percentages of alpha chain crosslinking compared to gels. In this example, a series of gels had a degree of cross linking of about 49%, while a series of foams made by the device of FIG. 3 had a degree of cross linking of about 40-45%, while a series of foams made by the device of FIG. 5 had a degree of cross-linking of about 40-45%.

Materials Used in the Mixer

The inline mixer is made from a polymeric material formed by sintering to define an integral porous structure. The lattice or matrix of polymeric material forms a plurality of essentially randomly-shaped, tortuous interconnected passageways through the mixer. The material of the inline mixer 36 may be selected, for example, from one or more of the following: polyethylene (PE), high density polyethylene (HDPE), polypropylene (PP), ultra high molecular weight polyethylene (UHMWPE), nylon, polytetrafluoroethylene (PTFE), polyvinylidenefluoride (PVDF), polyester, cyclic olefin copolymer (COC), thermoplastic elastomers (TPE) including EVA, polyetheretherketone (PEEK), glass, ceramic, metal, other polymer materials, or other similar materials. Inline mixers may also be made of a polymer material that contains an active powdered material such as carbon granules or calcium phosphate granules with absorbed molecules. Other types of materials are also possible. A sintered polypropylene material suitable for the embodiments described herein may be available from commercial sources, such as from Bio-Rad Laboratories, Richmond, Calif., United States, Porex Porous Products Group of Porex Manufacturing, Fairburn, Ga., United States, Porvair Technology, a Division of Porvair Filtration Group Ltd., of Wrexham, United Kingdom, including Porvair Vyon Porvent, PPF or PPHP materials, or MicroPore Plastics, Inc., of 5357 Royal Woods, Parkway, Tucker, Ga., U.S.A.

It is also possible that the inline mixer may be made of one or more materials having one or more characteristics that may assist mixing of the component streams. By way of example and not limitation, the material may be hydrophilic, which is material that absorbs or binds with water, or hydrophobic, a material which is essentially repels and does not bind with water. The material may also be oleophobic, i.e., resistant to absorption of oils and the like, and may have other desirable characteristics that enhance mixing of the components.

Additional Components

One or more additional component or agent may be pre-mixed with one or more of the components, such as the fibrinogen or thrombin, or both in the respective component container. Alternatively, an additional component or components may be stored in a separate container as a liquid or in a lyophilized form for mixing with one or more components during use of the foam mixer, the foam dispenser, or both the foam mixer and dispenser. The additional component or components may be stored in the same container as frozen separated liquids, the separation performed by a layer of frozen water. They may also be stored as separated layers of lyophilized fibrinogen and thrombin separated from each other because the water frozen layer separating the two active ingredient has been sublimed during freeze drying. In another method, they may be stored as a mixture of lyophilized fibrinogen and thrombin, or as a partially polymerized fibrin powder. In this case, when making fibrin foam, one syringe contains the component and a second syringe contains air or a diluent alone or containing any of the active components described above or below.

In an example, a device using two opposed single syringes (not shown) is used. A desired amount of a lyophilisate of fibrinogen is placed into a first syringe. An appropriate mixture of sterile water and air (diluent) is placed into a second, opposed syringe. The plunger on the second syringe is depressed, pushing the diluent into the first syringe with the fibrinogen lyophilisate. After allowing a certain amount of time for reconstitution, and when the fibrinogen is completely dissolved, the plunger on the first syringe is depressed, forming a fibrinogen foam by pushing the mixture into the second syringe. Several more transfers are then accomplished for thorough mixing to form a satisfactory fibrinogen foam. This process may also be used with one or more additives.

For a dispenser or mixer, such as in any of the above described embodiments, in which one or more agents are employed, the combined stream provides a sufficiently thoroughly mixed sealant or wound dressing, such as fibrin wound dressing, in which the antibiotic, drug, hormone, or other agent or agents are well dispersed throughout the sealant. Such antibiotic, drug, hormone, or other agent may allow controlled release over time to the applied working surface, for example, to aid in post-operative or surgical treatment. It is contemplated that various agents may be employed depending on the desired application and the combined fluid stream.

These components include Factor XIII, a calcium compound, human or animal or vegetal protein solutions containing collagen, oxidized collagen, growth factors, coagulation factors, fibronectin, plasminogen or plasminogen inhibitor or both plasminogen and plasminogen inhibitor. A plasminogen inhibitor is one which inhibits the conversion of plasminogen in plasmin, such as aprotinin, tranexanic acid, a2-antiplasmins, a2-macroglobulins, a2-antitrypsin, antithrombin, antistreptokinase, aminocapronic acid, tranexamic acid, Cl-esterase inhibitor, anti-urokinase, and the like. Components for activating the conversion of plasminogen into plasmin may also be used, such as t-PA, u-PA, streptokinase, alt­ephase, and the like, and albumin, casein, soya, and amino acids. These may be used in combination with mono-, di-, tri, and polysaccharides or mucoopolysaccharides. These may include carrageenan, agarose, cellulose, methylcarboxycellulose, chitin, chitosan, alginic acid, glycosaminoglycans, hyaluronic acid and chondroitin sulfate, or the derivatives thereof.

They may also be used with polyglycols or other glycols and high molecular weight alcohols, such as glycerol, ethylene glycol, 1,3-propanediol, propylene glycol, sorbitol, sorbitan, mannitol, diglycerol, butanediol, and urea, or mixtures thereof. Glycerol and propylene glycol are useful plasticizers, as are the esters of polyols, such as glycerol monoacetate and glycerol diacetate. Also useful are hydrophilic polymers that have a molecular weight of 1,000 Da to 15,000 Da, also between 2,000 and 5,000 Da. For example, glycol polymers, such as derivatives of polyethylene glycol (PEG), polyoxyethylenes, polymethylene glycols, polytrimethylene glycols and polyvinylpyrrolidones (PVP), and with povidone, per the Merck Index, 9th ed., p. 996, No. 7498. Derivatives of PEG, fungicides and bactericides such as Proxcel CRL, lysozyme, and foam stabilizers, may also be used. Surfactants, such an nonionic surfactants, cationic surfactants, anionic surfactants, and amphoteric surfactants, fatty acids, helianthinin and sunflower albumins (SFAs), egg white (albumen), fluorocarbon and hydrocarbon surfactants, may also be added, as may coloring agents, modifiers, and preservatives, natural cellulosic fiber, plasticizer, blowing agent, nucleating agent, metallic salt hydrate, and cross-linking reagents, and other property modifiers.

Synthetic coloring agents for contrast on the wound dressing may include azo dyes such as Amaranth, Ponceau 4R, Tartrazine, Sunset Yellow, Indigo Carmine. Natural coloring agents include xanthophyll, chlorophyll, and metallic oxides. As discussed above, biologically active substances may also be used to enhance binding or viscosity. These may include vascular endothelial growth factor [VEGF], endothelial cell growth factor (ECGF), basic fibroblast growth factor [bFGF], and bone morphogenic protein [BMP].

Starch, dextran or hyaluronic acid are also useful ingredients. Such starches can include corn starch, including maize, waxy maize, and high amylose corn starch, potato starch, sweet potato starch, wheat starch, rice starch, tapioca starch, sorghum starch, and a combination, hydroxyethyl starch, hydroxypropyl starch, carboxymethyl starch, acetylated high amylose starch, starch acetate, starch maleate, starch octenylsuccinate, starch succinate, starch phthalate, hydroxy-propylate high amylose starch, cross-linked starch, starch phosphates, hydroxypropyl distarch phosphate, cationic starch, starch propionamide, and combinations thereof.

Other additives may include radioprotective agents comprising at least one iodine containing organic compound (lodixanol), vitamins, hormones, steroid derivatives, antibiotics, vaccines, antiviral agents, antifungal agents, antiparasitic agents, antioxidants, antitumor agents, anticancer agents, toxins, enzymes, enzyme inhibitors, proteins, peptides, inorganic compounds (e.g., zinc, copper, selenium, calcium derivatives), neurotransmitters, lipoproteins, glycoproteins, immunomodulators, immunoglobulins and fragments thereof, contrast agents, fatty acid derivatives, nucleic acids (e.g., DNA, RNA fragments) and polynucleotides, biological tissues, including live tissues and cells from these tissues, milk, clupeine, lysozyme, thaumatin and monellin. In addition, micro-sized particles and nanoparticles or suspensions may be used for their antimicrobial or antibacterial properties, such as silver or titanium oxide particles, or other oligodymanic metals or compounds. Sulfonamide nanocrystals, or nanoparticles of other antibiotics, antimicrobials or other medicaments, may also be used.

Contrast agents may also be used, such as diatrizoate (meglumine), iodecol, iodixanol, iofratol, iogulamide, iohexyl, iomeprol, iopamidol, iopromide, iotrol, ioversol, ioxaglate and metrizamide and mixtures thereof. Also useful are calcium compounds, and other substances from the group consisting of tricalcium phosphate, alpha-tricalcium phosphate, beta-tricalcium phosphate, calcium phosphate, a polymorph of calcium phosphate, hydroxyapatite, calcium carbonate, calcium sulfate, polylactide, polyglycolide, polycaprolactone, polytrimethylene carbonate, and any combination thereof.

The gas used in embodiments can include air or one or more of the components of air, for example, nitrogen, oxygen, or carbon dioxide. Aqueous protein solutions (i.e., solutions containing globular proteins) are also used to form emulsions with oil phases. Such emulsions are used in manufactured foodstuffs such as mayonnaises and sauces. It is generally desirable that such emulsions should be stable during storage for long periods.

Thrombin Inhibitors

As noted above, once the foamed fibrinogen and the foamed thrombin are mixed, with a highly enlarged surface area, they react rapidly to form a fibrin foam in a very convenient and efficient manner. In some applications, it is desirable to inhibit this reaction, such as to allow the surgeon additional time for the procedure at hand or insure that the foamed fibrin is properly placed. Accordingly, inhibitors may be added to the thrombin portion of the components discussed above in order to delay the curing of the fibrin foam. One particularly useful type of inhibitor is an inhibitor that is photosensitive, i.e., the photosensitive compound delays curing until the compound is activated with light. Activation takes place when the fibrin foam is subjected to strong light or by irradiation with light of a certain wavelength. Of course, the photo-sensitive inhibitor must not be harmful to the patient, to the thrombin, or to the fibrin foam.

Such photo-sensitive inhibitors are disclosed in U.S. Pat. No. 5,318,524, the entire contents of which are hereby incorporated by reference, as though each word and disclosure were set forth herein, page for page and word for word. Examples of such photoinhibitors include, but are not limited to: 4-amidino-phenyl-2-hydroxy-4-diethylamino-alpha-methylcinnamate hydrochloride; a cinnamoyl derivative; and D-phenylalanyl-L-prolyl-L-arginine chloromethyl ketone. In previous experiments, an amount of inhibitor was added to the thrombin, which may then kept in the dark for long periods of time, even when mixed with fibrinogen. Upon exposure to light, the mixture reacts and forms fibrin. An amount effective to inhibit the reaction is used, and is then overcome by exposure to light. An alternative to speed up the reaction is to irradiate the foamed fibrin with light of a suitable wavelength, such as by irradiating fibrin foam, to which an effective amount of D-phenylalanyl-L-prolyl-L-argininechloromethylketone has been added, with a 350 nm wavelength light.

Thrombin Substitutes

While thrombin is clearly the predominant component used to react fibrinogen to form fibrin, other chemical species, known here as thrombin substitutes or clotting proteins, may also be used. For example, trisodium citrate has been added to a prothrombin complex (PTC) from human plasma to produce a thrombin substitute or clotting protein. See E. Shanbrom et al., *J. Thrombosis and Haemostasis,* 1 Suppl. 1 July 2003. In addition, other thrombin substitutes are disclosed in U.S. Pat. Appl. Publ. 2003/0146113, including p-aminoaniline derivatives, such as $R_1R_2$—N-phenyl-NH—CO-Arg-Pro-Gly-Tosyl, in which $R_1$ may be alkyl or hydrogen and in which $R_2$ may be hydrogen or hydroxalkyl. The phenyl group may also be a single-substituted phenyl, the substitution including halogen, alkoxy, or alkylthio. This molecule has at least a minimal protein structure, that is, a linear chain joined together by peptide bonds between the carboxyl and amino groups of adjacent amino acid residues. Other clotting proteins include such thrombin-like enzymes as salmonase precursor, snake venom thrombin-like enzymes (SVTLEs), gabonase, ancrod, batroxobin, bilineobin, bothrombin, calobin, catroxobin, cerastobin, crotalase, flavoxobin, gabonase, grambin, habutobin, okinaxobin I, okinaxobin II, stenoxobin, thromboxytin and prothrombin. In terms of their use in wound dressings, these clotting proteins, and others with similar structures, are clearly equivalent to thrombin, at least in their clotting effect. Fibrinogen can be from plasma (3 mg/ml), recombinant from autologous preparation (up to 35 mg/ml), plasma enriched in fibrinogen (10 mg/ml), or concentrate as for our fibrin sealant (up to 100 mg/ml). Of course, lower concentrations may used and clotting time compensated for by increasing the thrombin concentration.

Platelet Development Growth Factor (PDGF) and Bone Morphogenic Proteins (BMP)

It is also possible to add other agents, such as healing agents, antibiotics, drugs or hormones to one or more of the components. For example, additives such as Platelet Derived Growth Factor (PDGF), Bone Morphogenic Proteins (BMP), as modied bioactive fusion proteins, or Parathyroid Hormone (PTH), such as those manufactured for Kuros Biosurgery AG of Zurich, Switzerland, may be added to one of the fibrin-forming components, such as fibrinogen.

The self-assembly step mentioned above is enhanced if the mixture includes a growth factor, such as PDGF, especially PDGF that includes an additional amino acid sequence at one or both ends of the protein or peptide that constitutes the growth factor. The additional amino acid sequence is a transglutaminase substrate domain, i.e., a domain that crosslinks into the fibrin network during its formation in the presence of Factor XIII, thrombin, and a calcium source. The additional amino acid sequence is designed to contain an enzymatic cleavage site. This technology, known as TG-PDGF, enables the retention of a growth factor within a fibrin matrix during the process of wound healing. This technology was developed by Kuros Biosurgery AG of Zurich, Switzerland. As used herein, the term PDGF includes TG-PDGF.

As part of the healing process, cells grow through the matrix and remodel it. During the remodeling phase, the cells release enzymes which cleave the enzymatic degradation site in the additional amino acid sequence, thereby releasing the unmodified version of the growth factor or peptide. Subsequently, the released growth factors and peptides trigger the body's own healing mechanisms. Using this technology, even low doses of growth factors, peptides, or other bioactive factors show efficacy since diffusion or burst release is avoided. The fibrin matrix allows incorporation of other materials, such as cells or materials that increase mechanical stability of the fibrin, including calcium sources such as hydroxylapatite or calcium phosphate.

Testing was conducted while preparing formulations for wound dressing using varied concentrations of thrombin, as well as fibrinogen concentrations greater than 50 mg/ml. The testing included concentrations of fibrin stabilizing Factor XIII, also known as FXIII. The testing used FXIII concentrations greater than 0.5 IU/ml, and different concentrations of PDGF, such as 33, 100, and 300 µg/ml. Other concentrations, at least up to 1000 µg PDGF per ml may also be used.

Bone morphogenic proteins (BMP) may also be employed. By way of example, other agents include celluloses, such as hydroxypropylmethylcellulose, carboxylmethylcellulose and other celluloses, chitosan, photo-sensitive inhibitors of thrombin and thrombin-like molecules, self assembling amphiphile peptides designed to mimic aggregated collagen fibers (extracellular matrices), Factor XIII, cross-linking agents, pigments, fibers, polymers, copolymers, antibody, antimicrobial agent, agents for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, interferons, hormones, polysaccharides, genetic materials, proteins promoting or stimulating the growth and/or attachment of endothelial cells on the cross-linked fibrin, growth factors, growth factors for heparin bonding, and anti-cholesterol drugs. Collagen, osteoblasts, and the like, and mixtures thereof, may also be used.

For example, statins may be used, such as atorvastatin (Lipitor®), simvastatin (Zocor®, Lipex®, Simvar®), Pravastatin (Pravachol®), Fluvastatin (Vastin®, Lescol®). Local anesthetics may also be used, such as esters and amides. Esters include, but are not limited to, cocaine, procaine (Novocain®), benzocaine (Cetacaine®), tetracaine and chloroprocaine (Nescaine®). Amides include, but are not limited to, lidocaine, xylocaine, mepivacaine (Polocaine®, Carbocaine®), bupivacaine (Marcaine®), and etidocaine (Duranest® and Prilocaine®).

Further examples of such agents also include, but are not limited to, antimicrobial compositions, including antibiotics, such as tetracycline, ciprofloxacin, and the like; antimycogenic compositions; antivirals, such as gangcyclovir, zidovudine, amantidine, vidarabine, ribaravin, trifluridine, acyclovir, dideoxyuridine, and the like, as well as antibodies to viral components or gene products; antifungals, such as diflucan, ketaconizole, nystatin, fluconazole and glucanase, such as fluconazole 1 mg/ml in combination with glucanase 2.5 U/ml, and the like; and antiparasitic agents, such as pentamidine, and the like. Other agents may further include anti-inflammatory agents, such as alpha- or beta- or gamma-interferon, alpha- or beta-tumor necrosis factor, and the like, and interleukins.

Fibrinogen and thrombin are available commercially as fibrin glues such as BERIPLAST® from Aventis Behring, BIOCOL® from LFB, BOHELAL® from Kaketsuken, QUIXIL™ from Omrix, and HEMASEEL® from Hemacure. In addition, home made glues are known from automated systems such as VIVOSTAT™v, CRYOSEAL®, AUTO- SEAL™ and BIOCORAL®, as well as plasma derivative sealants such as FIBRx™ from Cryolife It should be understood that various changes and modifications to the embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method for forming a fibrin foam, the method comprising:
   combining a solution of fibrinogen with air by passing the fibrinogen and air through an inline mixer comprising a three-dimensional lattice defining a plurality of tortuous, interconnecting passages therethrough to form a first foam;
   combining a solution of a clotting protein with air by passing the clotting protein and air through an inline mixer comprising a three-dimensional lattice defining a plurality of tortuous, interconnecting passages therethrough to form a second foam; and
   mixing the first and second foams to form a fibrin foam, wherein the fibrin foam has a viscosity sufficient for a thin coating of the fibrin foam to adhere to a vertical surface.

2. The method of claim 1, wherein the clotting protein is selected from the group consisting of thrombin, a PTC-derived thrombin substitute, and a p-aminoaniline-based protein.

3. The method of claim 1, further comprising mixing at least one of the solutions with a therapeutic amount of a calcium-containing compound, an agent, a drug, an antibiotic, or a hormone.

4. The method of claim 1, wherein a rate of formation of the fibrin foam is constant in a temperature range from about 15° C. to about 37° C.

5. The method of claim 1, further comprising inhibiting the forming of the fibrin foam by adding an effective amount of a photosensitive inhibitor to the solution of clotting protein.

6. The method of claim 1, further comprising lyophilizing the fibrin foam to form a lyophilisate, and optionally grinding the fibrin foam or the lyophilisate into a powder.

7. The method of claim 6, further comprising reconstituting the fibrin foam by mixing with water or a water solution and optionally adding an additional component.

8. The method of claim 1, wherein the mixing step includes mixing the first foam with the second foam by passing the first foam and second foam through an inline mixer comprising a three-dimensional lattice defining a plurality of tortuous, interconnecting passages therethrough to form a fibrin foam.

* * * * *